(12) United States Patent
Spenciner

(10) Patent No.: US 10,426,596 B2
(45) Date of Patent: Oct. 1, 2019

(54) TISSUE FIXATION SYSTEM WITH AUXILIARY PLATE

(71) Applicant: DePuy Mitek, LLC, Raynham, MA (US)

(72) Inventor: David B. Spenciner, North Attleboro, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 226 days.

(21) Appl. No.: 15/670,020

(22) Filed: Aug. 7, 2017

(65) Prior Publication Data

US 2017/0333178 A1    Nov. 23, 2017

Related U.S. Application Data

(62) Division of application No. 14/039,494, filed on Sep. 27, 2013, now Pat. No. 9,750,599.

(51) Int. Cl.
*A61F 2/08* (2006.01)
*A61B 17/04* (2006.01)
(Continued)

(52) U.S. Cl.
CPC ........ *A61F 2/0811* (2013.01); *A61B 17/0401* (2013.01); *A61F 2/2846* (2013.01);
(Continued)

(58) Field of Classification Search
CPC ............ A61B 17/7053; A61B 17/7022; A61B 17/1691; A61B 17/1789; A61B 17/8076; A61B 17/823; A61B 17/82; A61B 17/0401; A61B 17/1728; A61B 17/58; A61B 17/7044; A61B 17/7058; A61B 17/0466; A61B 2017/0404; A61B 2017/0403; A61B 2017/0406; A61B 2017/0414; A61B 2017/042; A61B 2017/0422; A61B 2017/0424; A61B 2017/0438; A61B 2017/0446; A61B 2017/0448; A61B 2017/0459; A61B 2017/0496; A61B 18/14; A61B 2018/0063; A61B 2019/261; A61F 2/0811; A61F 2/08; A61F 2/0805; A61F 2002/0852; A61F 2002/0817; A61F 2002/0823; A61F 2002/0829;
(Continued)

(56) References Cited

U.S. PATENT DOCUMENTS 4,172,330 A    10/1979 Kao
5,306,301 A    4/1994 Graf
(Continued)

FOREIGN PATENT DOCUMENTS

CN    101150995 A    3/2008
CN    102481187 A    5/2012
(Continued)

*Primary Examiner* — Christopher L Templeton
*Assistant Examiner* — Chima U Igboko

(57) ABSTRACT

A tissue fixation system provides a primary fixation plate with a depending graft retention loop and a longer auxiliary fixation plate which fits to the primary fixation plate via upwardly projecting pegs which fit into suture holes in the primary fixation plate. The system has particular utility in cortical fixation procedures in which a graft channel is over-drilled and a longer fixation plate is indicated.

3 Claims, 4 Drawing Sheets

(51) Int. Cl.
*A61F 2/28* (2006.01)
*A61F 2/30* (2006.01)

(52) U.S. Cl.
CPC .......... *A61B 2017/0404* (2013.01); *A61B 2017/0414* (2013.01); *A61B 2017/0464* (2013.01); *A61F 2002/087* (2013.01); *A61F 2002/0823* (2013.01); *A61F 2002/0852* (2013.01); *A61F 2002/0882* (2013.01); *A61F 2002/285* (2013.01); *A61F 2002/30126* (2013.01)

(58) Field of Classification Search
CPC ...... A61F 2002/0835; A61F 2002/0847; A61F 2002/0858; A61F 2002/0864; A61F 2002/087; A61F 2002/0876
See application file for complete search history.

(56) References Cited

U.S. PATENT DOCUMENTS

| | | |
|---|---|---|
| 5,645,588 A | 7/1997 | Graf |
| 5,797,932 A | 8/1998 | Min et al. |
| 6,283,996 B1 | 9/2001 | Chervitz |
| 6,517,579 B1 | 2/2003 | Paulos |
| 6,833,005 B1 | 12/2004 | Mantas |
| 7,144,413 B2 | 12/2006 | Wilford et al. |
| 8,246,660 B2 | 8/2012 | Boris et al. |
| 8,323,338 B2 * | 12/2012 | LeBeau ............ A61B 17/0401 606/232 |
| 8,568,483 B2 | 10/2013 | Coppes et al. |
| 2004/0044366 A1 * | 3/2004 | Bonutti ............ A61B 17/0487 606/232 |
| 2007/0213582 A1 * | 9/2007 | Zollinger ........... A61B 17/0401 600/37 |
| 2009/0318830 A1 | 12/2009 | George et al. |
| 2010/0262185 A1 | 10/2010 | Gelfand |
| 2012/0310279 A1 | 12/2012 | Sikora |
| 2013/0090687 A1 | 4/2013 | Lebeau |
| 2013/0096678 A1 | 4/2013 | Denham |

FOREIGN PATENT DOCUMENTS

| | | |
|---|---|---|
| EP | 2476378 A1 | 7/2012 |
| EP | 2586380 A1 | 5/2013 |
| EP | 2777513 A1 | 9/2014 |
| JP | 2010-515535 | 5/2010 |
| WO | WO 2007073563 A2 | 6/2007 |

* cited by examiner

US 10,426,596 B2

TISSUE FIXATION SYSTEM WITH AUXILIARY PLATE

CROSS REFERENCE TO RELATED APPLICATIONS

This application is a divisional application of U.S. patent application Ser. No. 14/039,494, entitled TISSUE FIXATION SYSTEM WITH AUXILIARY PLATE, filed Sep. 27, 2013, the entire contents of which are hereby incorporated by reference.

BACKGROUND

The present invention relates to tissue fixation plate system and more specifically to such systems having a primary fixation plate with a depending graft retention loop and a longer auxiliary fixation plate.

Tissue fixation plates fix tissue to bone adjacent a bone tunnel. One common usage occurs in Anterior Cruciate Ligament (ACL) reconstruction. A bone tunnel is formed through a femur. It comprises a graft channel wide enough to accommodate a replacement graft tissue and terminates in a smaller passing channel that exits through the cortical bone and is wide enough to pass the fixation plate. The graft is carried by a loop depending from the fixation plate and the plate is guided lengthwise up through the bone tunnel whereupon its orientation is flipped approximately ninety degrees to rest against the surface of the femur and be thus prevented from passing back through the tunnel. Examples of such flipping-type fixation devices are disclosed in U.S. Pat. Nos. 5,306,301 and 5,645,588 incorporated herein by reference.

If the graft channel is drilled too deeply there may be no passing channel or insufficient bone thickness to support a preferred size of fixation plate. A surgeon may also desire to prepare a single diameter bone tunnel. In each case a larger fixation plate will be required for proper fixation. An expanded size accessory plate is typically employed having a length exceeding that of the primary fixation plate and having an upper recess into which the primary fixation plate fits.

Current accessory plates are difficult to use because of the difficulty in attaching them seamlessly to the primary fixation plate. Often the graft must first be removed from the graft loop so that the graft loop can be threaded into a hole through the accessory plate that accepts the loop. Then, the graft must be re-loaded on the graft loop prior to the construct being used. Also, the existing plates do not tend to interconnect well.

Other solutions include simply using a larger fixation plate, but again, the graft must be offloaded from the original loop and then loaded onto the second plate's graft loop.

SUMMARY OF THE INVENTION

The present innovation improves on the prior art by reducing the number of steps and allowing the graft to remain on the loop while loading the accessory plate onto the construct. Also, there is a perception among many surgeons that it is desirable to maintain an axial load on the graft prior to insertion in the body to remove stretch. The present innovation improves on prior art by permitting the graft to remain in its loaded configuration for longer than other technologies.

A tissue fixation device according to the present invention comprises a first fixation plate comprising an elongated body having a first end and a second end with a length therebetween. A first suture aperture is provided at the first end, and a central graft support loop depending from the body. A second fixation plate receives the first fixation plate and comprises an upper surface having a first peg projecting upwardly therefrom through the first suture aperture of the first fixation plate. The second fixation plate has a length exceeding the length of the first fixation plate.

Preferably, the first fixation plate further comprises a second suture aperture and the second fixation plate further comprises a second peg projecting upwardly therefrom through the second suture aperture of the first plate.

Preferably, the length of the second fixation plate exceeds the length of the first fixation plate by at least 15 percent.

Preferably, the length of the second fixation plate exceeds the length of the first fixation plate by at least 65 percent.

In one aspect of the invention, the second fixation plate further comprises a first suture receiving aperture with a first suture therethrough and a second suture receiving aperture with a second suture therethrough.

In one aspect of the invention the second fixation device has a first suture receiving aperture with a suture therethrough which comprises a cannulation through the first peg.

Preferably, the second fixation plate has a lower surface opposite its upper surface and the graft support loop depends below the second fixation plate lower surface.

Preferably, the first peg fits closely within the first suture aperture of the first fixation plate. The first peg can be provided to fit with a compression fit within the first suture aperture of the first fixation plate to hold together the first fixation plate and the second fixation plate.

In one aspect of the invention the first fixation plate and second fixation plate interlock with each other. The interlocking can comprise a snap-fit engagement between the first fixation plate and the second fixation plate.

In one aspect of the invention the second fixation plate further comprises a side opening slot through which depends the graft support loop. The second fixation plate could comprise a pair of side opening slots with a separator in-between, and with the separator passing through the graft support loop laterally and the graft support loop depending downwardly through the side opening slots.

A method according to the present invention provides for anchoring a tissue graft to bone. The method comprising the steps of: preparing a bone tunnel through a bone; affixing a first fixation plate to a second fixation plate to form a construct, the first fixation plate comprising an elongated body having a first end and a second end with a length therebetween, a first suture aperture at the first end, and a central graft support loop depending therefrom, the second fixation plate receiving the first fixation plate and comprising an upper surface having a first peg projecting upwardly therefrom through the first suture aperture of the first fixation plate and wherein the second fixation plate has a length exceeding the length of the first fixation plate; affixing the tissue graft to the graft support loop; passing the construct lengthwise through the bone tunnel and then reorienting the construct to place the lower plate lower surface against the bone adjacent the bone tunnel with the graft support loop and graft depending downwardly into the bone tunnel.

Preferably, the first fixation plate further comprises a second suture aperture and the second fixation plate further comprises a second peg projecting upwardly therefrom through the second suture aperture.

Preferably, a suture affixed to the second fixation plate is used to pass the construct through the bone tunnel. The suture can be first removed from the first fixation plate and affixed to the second fixation plate. In one aspect of the invention, the suture is passed through the first peg.

DETAILED DESCRIPTION

Figure 1:
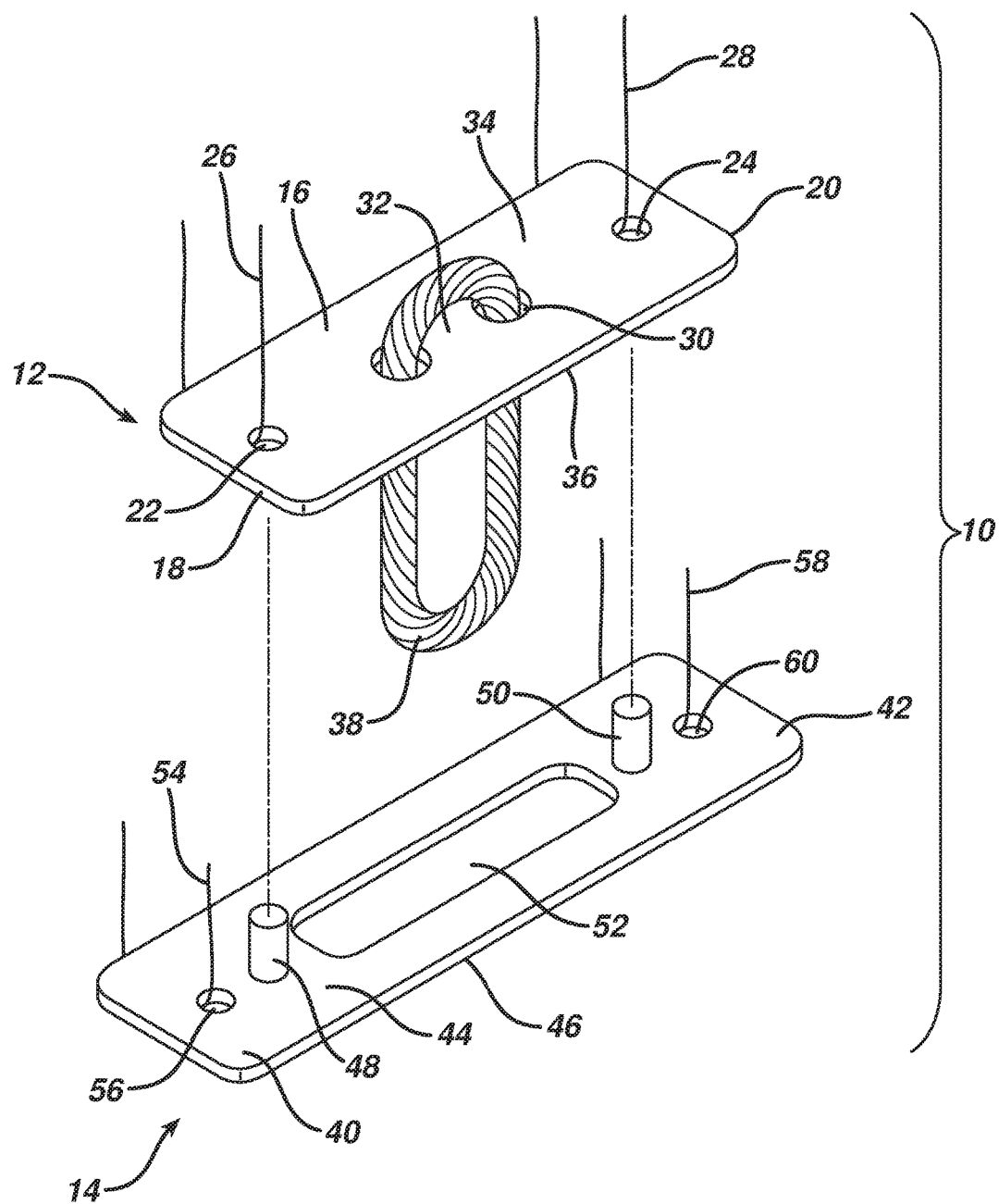
FIG. 1 is an exploded perspective view of a tissue fixation device according to the present invention.

FIG. 1 illustrates a tissue fixation device 10 according to the present invention. It comprises in gross a primary fixation plate 12 and an auxiliary fixation plate 14 which is longer than the primary fixation plate 12. The primary fixation plate 14 can be used by itself to provide fixation and when a longer length is desired it can be used with the auxiliary fixation plate 14 to form the fixation device 10 having a length exceeding that of the primary fixation plate 12.

A typical dimension for the primary fixation plate when used in ACL reconstruction would be about 4 mm wide by 12 mm long by 1 mm thick. Complimentary dimensions on the auxiliary fixation plate 14 in such case would be between about 14 mm to 26 mm long with a width of 4 mm matching that of the primary fixation plate or slightly wider, and a thickness of about 2 mm or as needed to meet the strength requirements. The dimensions can be varied to accommodate different sized patients and for different procedures. The length of the auxiliary plate 14 exceeds that of the primary fixation plate 12, preferably by between about 15% and 115% and most preferably by about 67%. Preferably they are formed of surgical grades of titanium or stainless steel or other biocompatible material having sufficient strength and rigidity.

The primary fixation plate 12 comprises an elongated body 16 having a first end 18 and a second end 20 with a first suture aperture 22 at the first end 18 and a second suture aperture 24 at the second end 20. A first guiding suture 26 is received through the first suture aperture 22 and a second guiding suture 28 is received through the second suture aperture 24. A pair of central apertures 30, having a bridge 32 therebetween, passes through the body 16 from an upper surface 34 to a lower surface 36 thereof and carries a flexible graft support loop 38 which depends from the body 16. The graft support loop 38 shown is a continuous loop of woven fibers but other configurations are possible including adjustable size loops.

Figure 2:
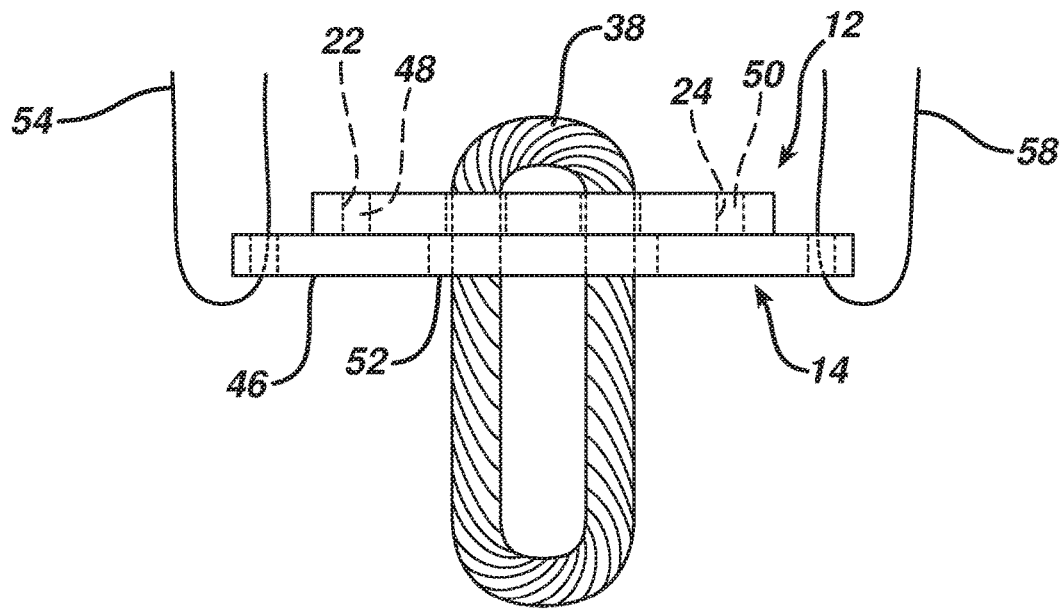
FIG. 2 is a side elevation view showing the tissue fixation device of FIG. 1.

The auxiliary fixation plate 14 is longer than and adapted to fit together with the primary fixation plate 12. It has a first end 40, second end 42, upper surface 44 and lower surface 46. A first peg 48 projects upwardly from the upper surface 44 and fits closely within the first suture aperture 22 of the primary fixation plate 12. A second peg 50 projects upwardly from the upper surface 44 and fits closely within the second suture aperture 24. An elongated central aperture 52 is sized to receive the loop 38 therethrough so that the when the primary fixation plate 12 and auxiliary fixation plate 14 are fitted together with the pegs 48 and 50 received through the suture apertures 22 and 24 the loop 38 depends downwardly through the aperture 52 to depend below the lower surface 46 of the auxiliary fixation plate 14 (see FIG. 2). The central aperture 52 can be sized to allow the primary fixation plate 12 to be passed upwardly therethrough so that it can be affixed to the auxiliary fixation plate 14 with a graft (not shown in FIGS. 1 and 2) attached to the loop 38.

A first guiding suture 54 is received through a first suture aperture 56 near the first end 40 of the auxiliary fixation plate 14 and a second guiding suture 58 is received through a second suture aperture 60 at the second end 42. The auxiliary plate 14 can be provided with only the suture apertures 56 and 60 and without the guiding sutures 54 and 58 in which case the guiding sutures 26 and 28 from the primary fixation plate can be removed and threaded through the suture apertures 56 and 60 in the auxiliary plate. If the auxiliary fixation plate 14 has its own sutures 54 and 58 then the guiding sutures 26 and 28 of the primary fixation plate 12 would be removed and discarded when used with the auxiliary fixation plate 14. This would negate the need to rethread these sutures 26 and 28 during a procedure.

Figure 3:
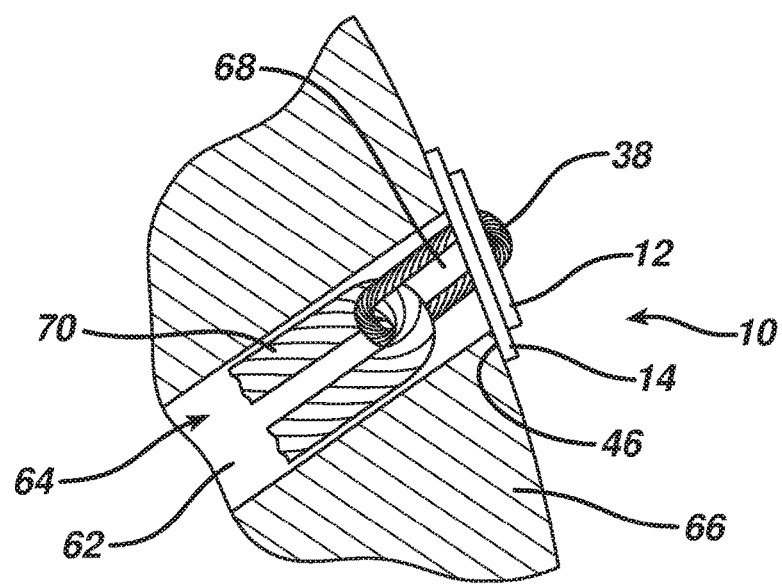
FIG. 3. Is a side elevation view in cross-section showing the tissue fixation device of FIG. 1 in use in a bone.

Turning now also to FIG. 3, a typical use for the auxiliary fixation plate 14 is when a graft channel 62 in a bone tunnel 64 is drilled too deeply through a bone 66 such as a femur leaving a short passing channel 68 (or no passing channel 68 if the graft channel 62 is completely overdrilled) and thus leaving insufficient bone 66 to support the primary fixation plate 12 by itself. The added length of the auxiliary plate 14 allows it to sit securely atop adjacent bone 66 and provide a secure repair.

After a surgeon determines the need for the auxiliary fixation plate 14 the auxiliary plate is affixed to the primary fixation plate 12. If a graft 70 is already attached to the loop 38 of the primary fixation plate 12 it need not be removed. The primary fixation plate 12 is passed upwardly through the central aperture 52 with its sutures 26 and 28 already removed and the pegs 48 and 50 of the auxiliary fixation plate 14 fitted into the empty suture apertures 22 and 24 of the primary fixation plate 12 with the loop 38 depending from the thus formed construct of the tissue fixation device 10. This construct is then passed lengthwise up through the bone tunnel 64 as would have been the primary fixation plate 12 but employing the sutures 54 and 58 of the auxiliary fixation plate 14. It is then reoriented to lay flat with the auxiliary fixation plate lower surface 46 bearing against the bone 66 and the loop 38 and graft 70 depending down into the bone tunnel 64, after which the guiding sutures 54 and 58 can be removed. For an ACL reconstruction an opposite end of the graft 70 would be fixed into a tibial tunnel (not shown).

Figure 4A:
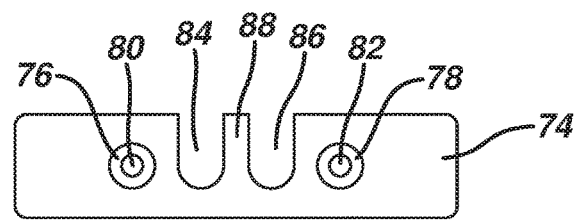
FIG. 4A is a top plan view of an auxiliary plate of an alternative embodiment of a tissue fixation device according to the present invention.
Figure 4B:
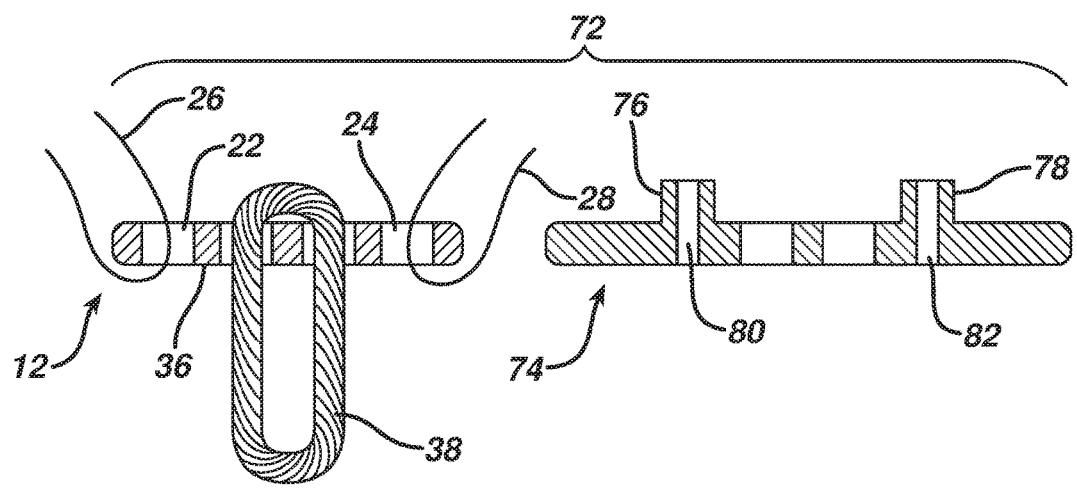
FIG. 4B is an exploded side elevation view in cross-section of the tissue fixation device of FIG. 4A.
Figure 4C:
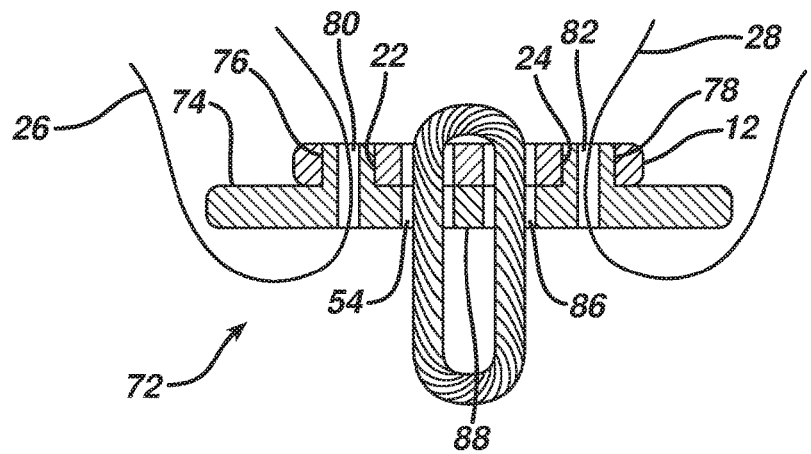
FIG. 4C is a side elevation view in cross-section of the tissue fixation device of FIG. 4B.

FIGS. 4A to 4C illustrate an alternative embodiment of a tissue fixation device 72 according to the present invention. It comprises the primary fixation plate 12 with an alternative auxiliary fixation plate 74 which has a structure similar to the auxiliary fixation plate 14 with several alternative features which can be employed together as shown here or separately. It differs in having first and second pegs 76 and 78 with respective first and second cannulations 80 and 82 extending axially therethrough and which replace the separate first and second suture apertures 56 and 60 of the auxiliary fixation plate 14. The first and second guiding sutures 26 and 28 can then be located at the same location with respect to the primary fixation plate 12 as its normal operation and their path through both the primary fixation plate 12 and auxiliary fixation plate 74 help to hold these two structures together.

It is contemplated that the sutures 26 and 28 would be repurposed from the primary fixation plate 12 to the cannulated pegs 76 and 78 and to this end the auxiliary fixation plate 74 can be provided with suture threaders (not shown) such as an elongated wire with a distal suture capture kite threaded therethrough to simplify the task of rethreading the sutures 26 and 28. Alternatively, the pegs 76 and 78 can be preloaded with new sutures in disposable holder plugs (not shown) in the cannulations 80 and 82 which can assist in completing the threading of the new sutures after the primary and auxiliary fixation plates 12 and 74 are configured together.

The auxiliary fixation plate 74 also differs from the first embodiment by having instead of the single enclosed, elongated central aperture 52, first and second side facing slots 84 and 86 with a dividing tang 88 formed therebetween. This allows the loop 38 to be loaded from the side into the slots 84 and 86 with the tang inserted through the loop 38.

To hold the auxiliary fixation plate 74 firmly to the primary fixation plate 12 it may be desirable to have an interlocking feature such as a snap-fit engagement between these two parts. For instance, each peg 76 and 78 could be provided with a slight distal and radial lip and one or more axial slots (not shown) so that they compress and reduce in diameter slightly as they are loaded into the suture apertures 22 and 24 and then as the lip passes past the body 16 the pegs spring back to lock the parts together. The parts need not have a snap-fit but could just have a sufficient interference fit to hold them together and thereby accomplish a similar objective.

Figure 5A:
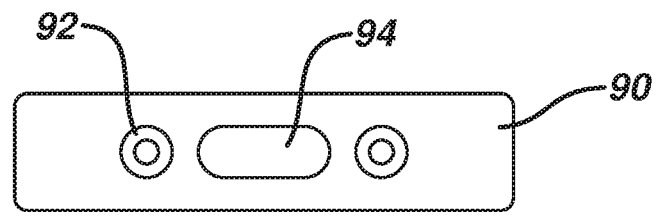
FIGS. 5A to 5C are top plan views of alternative embodiments of auxiliary tissue fixation plates according to the present invention.
Figure 5B:
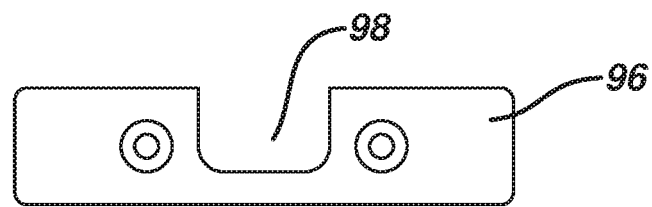
Figure 5C:
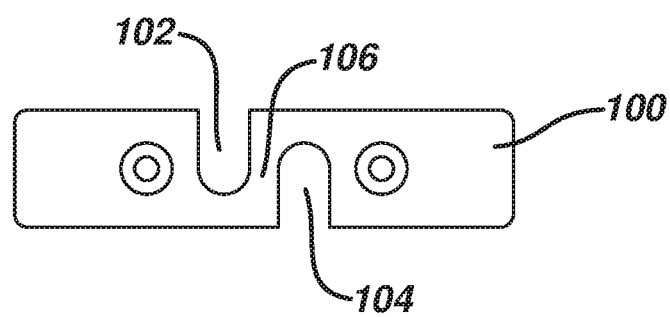

FIGS. 5A to 5C show three alternatives to the auxiliary fixation plate 74 for use with the primary fixation plate 12 of FIG. 1. FIG. 5A shows a plate 90 having cannulated pegs 92 and a single central aperture 94 for receipt of the loop 38. FIG. 5B shows a plate 96 having a single side-loading slot 98 for receipt of the loop 38. FIG. 5C shows a plate 100 having a pair of opposed side-loading slots 102 and 104 with a bridge 106 therebetween. The plate 100 would be passed partly through the loop 38 and rotated to load it into the slots 102 and 104.

While the invention has been particularly described in connection with specific embodiments thereof, it is to be understood that this is by way of illustration and not of limitation, and that the scope of the appended claims should be construed as broadly as the prior art will permit.

What is claimed is:

1. A method of anchoring a tissue graft to bone comprising the steps of:
    preparing a bone tunnel through a bone;
    affixing a first fixation plate to a second fixation plate to form a construct, the first fixation plate comprising an elongated body having a first end and a second end with a length therebetween a first suture aperture at the first end, and a central graft support loop depending therefrom, the second fixation plate receiving the first fixation plate and comprising an upper surface having a first peg projecting upwardly therefrom through the first suture aperture of the first fixation plate and wherein the second fixation plate has a length exceeding the length of the first fixation plate;
    affixing the tissue graft to the graft support loop;
    passing the construct lengthwise through the bone tunnel and then reorienting the construct to place a lower surface of the second plate against the bone adjacent the bone tunnel with the graft support loop and graft depending downwardly into the bone tunnel; and
    wherein a suture affixed to the second fixation plate is used to pass the construct through the bone tunnel, wherein the suture is passed through the first peg.

2. A method according to claim 1 wherein the first fixation plate further comprises a second suture aperture and the second fixation plate further comprises a second peg projecting upwardly therefrom through the second suture aperture.

3. A method according to claim 1 wherein the suture is removed from the first fixation plate and affixed to the second fixation plate.

* * * * *